(12) United States Patent
Gehman et al.

(10) Patent No.: US 6,871,537 B1
(45) Date of Patent: Mar. 29, 2005

(54) LIQUID FLOW SENSOR THERMAL INTERFACE METHODS AND SYSTEMS

(75) Inventors: Richard W. Gehman, Freeport, IL (US); Richard A. Alderman, Freeport, IL (US); Brian D. Speldrich, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/713,497

(22) Filed: Nov. 15, 2003

(51) Int. Cl.[7] .................................................. G01F 1/68
(52) U.S. Cl. .................................................. 73/204.26
(58) Field of Search ........................ 73/204.26, 204.25, 73/204.11; 136/255; 257/77

(56) References Cited

U.S. PATENT DOCUMENTS

| | | | |
|---|---|---|---|
| 4,478,076 A | 10/1984 | Bohrer | 73/204 |
| 4,478,077 A | 10/1984 | Bohrer et al. | 73/204 |
| 4,548,078 A * | 10/1985 | Bohrer et al. | 73/204.22 |
| 4,555,939 A | 12/1985 | Bohrer et al. | 73/198 |
| 4,856,328 A | 8/1989 | Johnson | 73/202 |
| 5,393,351 A * | 2/1995 | Kinard et al. | 136/225 |
| 5,708,213 A | 1/1998 | Batey | 73/861.32 |
| 5,818,071 A * | 10/1998 | Loboda et al. | 257/77 |
| 5,852,247 A | 12/1998 | Batey | 73/861.17 |
| 6,502,459 B1 | 1/2003 | Bonne et al. | 73/170.11 |
| 6,523,403 B1 * | 2/2003 | Fuertsch et al. | 73/204.26 |
| 6,553,808 B2 | 4/2003 | Bonne et al. | 73/24.01 |

OTHER PUBLICATIONS

"What are 3M Z–Axis Adhesive Films?" Nov. 15, 2003 http://www.3m.com/us/mfg_industrial/adhesives/html/what_are_z–axis.jhtml.

* cited by examiner

*Primary Examiner*—Edward Lefkowitz
*Assistant Examiner*—Jewel V. Thompson
(74) *Attorney, Agent, or Firm*—Kris T. Fredrick; Kermit D. Lopez; Luis M. Ortiz (57) ABSTRACT

A sensor method and system are disclosed. A fluid flow sensor can be provided, which measures the thermal conductivity of a fluid. The sensor itself can be configured to comprise one or more sensing element associated with a sensor substrate. A heater can be associated with said sensor wherein said heater provides heat to said fluid. A film component can also be provided that that isolates said fluid from said heater and said sensor, such that said film component conducts heat in a direction from said heater to said sensor, thereby forming a thermal coupling between said sensor, said heater and said fluid, which permits said sensor to determine a composition of said fluid by measuring thermal conductivity thereof without undesired losses of heat in other directions. The film component can be configured on or in the shape of a tubing or a flow channel.

22 Claims, 5 Drawing Sheets

LIQUID FLOW SENSOR THERMAL INTERFACE METHODS AND SYSTEMS

TECHNICAL FIELD

Embodiments are generally related to sensing methods and systems. Embodiments are also related to fluid flow sensors. Embodiments are additionally related to flow channels and tubing devices utilized in association with fluid flow sensors.

BACKGROUND OF THE INVENTION

Sensors have been used to measure flow rates in various medical, process, and industrial applications, ranging from portable ventilators supplying anesthetizing agents to large-scale processing plants in a chemical plant. In these applications, flow control is an inherent aspect of proper operation, which is achieved in part by using flow sensors to measure the flow rate of a fluid within the flow system. In many flow systems, e.g., fuel cell flow systems containing a binary mixture of methanol and water, the chemical composition of the fluid may change frequently.

A flow system is often required to flow more than one fluid having different chemical and thermo physical properties. For example, in a semiconductor processing system that passes a nitrogen-based gas, the nitrogen-based gas may at times be replaced by a hydrogen-based or helium-based gas, depending on the needs of the process; or in a natural gas metering system, the composition of the natural gas may change due to non-uniform concentration profiles of the gas.

Fluid flow sensors are thus important in a variety of applications. It is often necessary to determine the composition of a fluid utilizing a liquid or fluid flow sensor. One method for determining the composition of the fluid is to measure its thermal conductivity and compare the resulting value to a standard value. Measurements can be obtained by measuring power transferred from a heater to the fluid. In many cases, the fluid should not come into contact with the sensor and/or associated heater due to material incompatibility, explosion proof applications, or even medical hazards. A compatible material should therefore be placed between the fluid and the sensor and/or heater. Such material, however, typically dissipates power away from the fluid and the sensor, thereby reducing the thermal efficiency and therefore the signal quality. What is needed, therefore, is an enhanced sensor configuration that can overcome the aforementioned drawbacks.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide an improved sensor system and method.

It is another aspect of the present invention to provide for an improved material or tubing for conducting heat in a fluid flow sensor for thermal conductivity measurements of fluid.

It is yet a further aspect of the present invention to provide a film that isolates a heater from a fluid flow sensor for energy conservation and improved measurements thereof.

It is an additional aspect of the present invention to provide an improved fluid flow sensor for measuring the composition of a fluid.

The aforementioned aspects of the invention and other objectives and advantages can now be achieved as described herein. A sensor method and system are disclosed. A fluid flow sensor can be provided, which measures the thermal conductivity of a fluid. The sensor itself can be configured to comprise one or more sensing element associated with a sensor substrate. A heater can be associated with said sensor wherein said heater provides heat to said fluid. A film component can also be provided that that isolates said fluid from said heater and said sensor, such that said film component conducts heat in a direction from said heater to said sensor, thereby forming a thermal coupling between said sensor, said heater and said fluid, which permits said sensor to determine a composition of said fluid by measuring thermal conductivity thereof without undesired losses of heat in other directions. The film component can be configured on or in the shape of a tubing or a flow channel.

Additionally, the film component or tubing can be composed of at least one wall having a wall thickness thereof, wherein a plurality of thermally conductive particles are dispersed within said wall or walls of said tubing or flow channel. The plurality of thermally conductive particles preferably possesses a particle diameter that is approximately equivalent to or less than said wall thickness. Such plurality of thermally conductive particles also possesses a high thermal conductivity and a low electrical conductivity.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate at least one embodiment of the present invention and are not intended to limit the scope of the invention.

Figure 1:
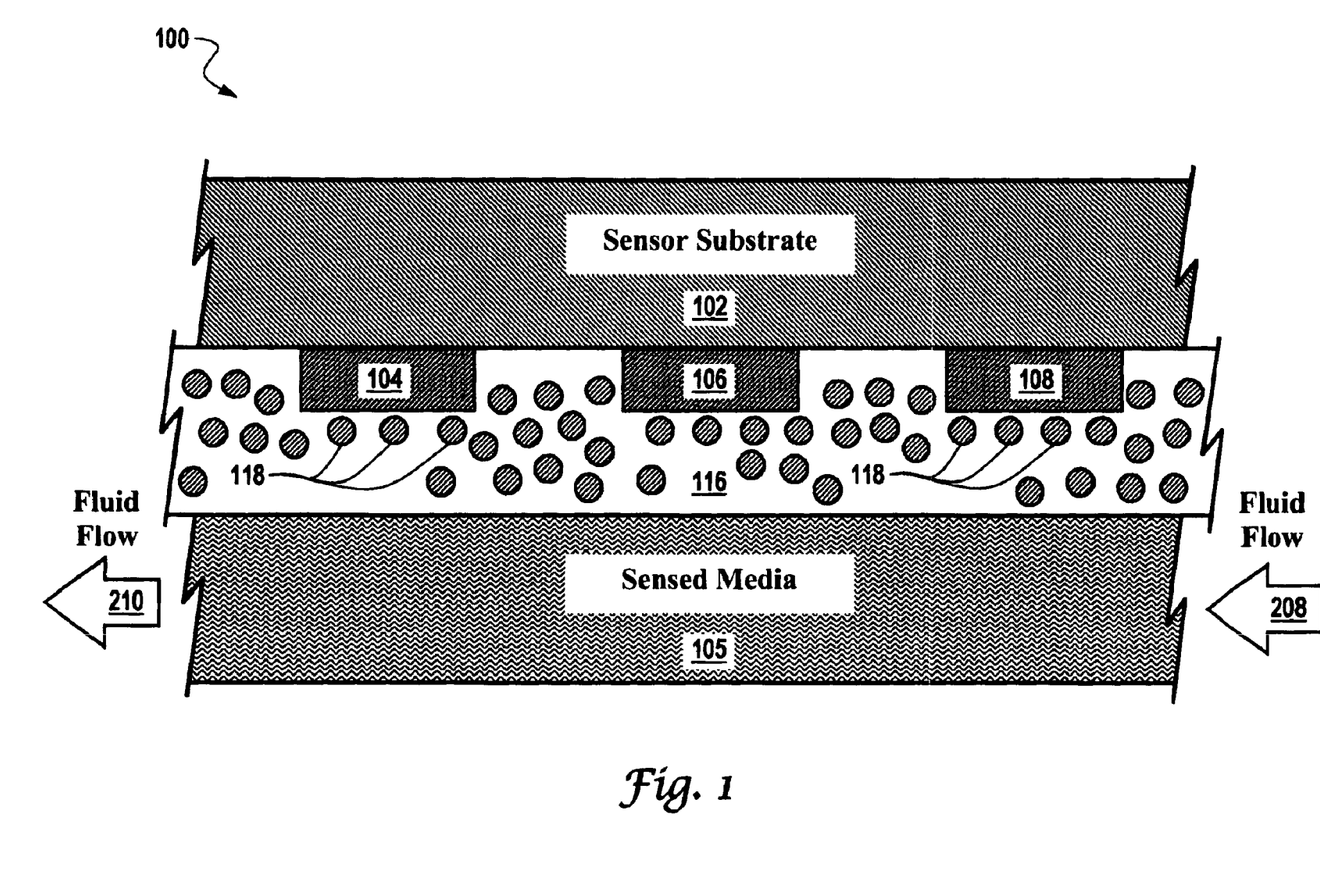
FIG. 1 illustrates a block diagram of a sensor system, which can be implemented in accordance with an embodiment of the present invention.

FIG. 1 illustrates a block diagram of a sensor system 100, which can be implemented in accordance with an embodiment of the present invention. System 100 comprises a low thermal conductivity tubing 116 with a plurality of thermally conductive particles 118 within the walls of tubing 116. A plurality of sensing elements 104 and 108 can be disposed along a sensor substrate 102 opposite sensed media 105. Although a single sensor substrate 102 and sensed media 105 are depicted in system 100 of FIG. 1, it can be appreciated that alternative embodiments thereof can be configured to function with one or more such sensor substrates and one or more sets of associated sensor elements.

Sensed media 105 can be, for example, a liquid such as saline or another equivalent medical fluid utilized in medical applications. The fluid flow, represented by arrows 208 and 210 is generally co-linear with the sensed media 105. Element 106 can be, in a particular embodiment, a heater or a sensing element co-located with sensing elements 104 and 108. Elements 104, 106 and 108 can thus be implemented as sense resistors. Assuming that element 106 is a heater, heat can then transfer from heater 106 through thermally conductive particles 118 to the fluid sensed (i.e., sensed media 105).

The heat can then be conducted through the fluid to other conductive particles that are in contact with the sensing resistors or sensing elements 104, 108. The heat is finally conducted through such particles to elements 104 and 108 at which point the heat is sensed and a flow signal generated. It can be appreciated that although FIG. 1 illustrates the use of element 106 (e.g. a heater and/or sensing element), the configuration of FIG. 1 can be implemented without element 106, in which case elements 104 and 108 can implemented as self-heated elements, which can cool at different rates dependent on flow.

When there is no flow, however, elements 104 and 108 can obtain the same amount of heat and their signal difference becomes a zero value. If flow is present from right to left, as indicated by arrows 208 to 210, then the sensor or sensing element 108 is cooler than that of sensing element 104. A difference signal is therefore present, which is proportional to mass flow. Note that in FIG. 1, fluid flow can be bi-directional. In one implementation, fluid flow can be from right to left, respectively from arrow 208 to 210. In an alternative embodiment, fluid flow can be from left to right, respectively from arrow 211 to 213.

Each particle diameter of the plurality of thermally conductive particles 118 is approximately equivalent to the wall thickness of the walls of tubing 116. Such particles are gathered in a high percentage, such that they do not generally come into physical contact with one another. Thus, thermal conduction radially is very much higher than thermal conductivity in the longitudinal or circumferential directions thereof. The base tubing 116 can be formed from a low thermal conductivity non-silicone plastic material. In alternative embodiment, silicone material may function, but will have a lower efficiency due to its relatively high thermal conductivity. Thus, non-silicone plastic material is preferential.

The particles 118 possess a high thermal conductivity and a low electrical conductivity. Particles 118 can be formed from materials such as, but not limited to, diamond or crystalline ceramic material. Anodized aluminum or other oxidized metals can be utilized to form such particles 118. Electrically conductive particles can also be utilized in place of particles 118, but are generally not desired because such particles may react with fluid flowing through tubing 116 or leak electricity into undesired areas.

Fluid flow through sensed media 105 is generally depicted in FIG. 1 by arrows 208 and 210. A heater 106 can provide heat, as indicated by arrows 106 and 108. In order to determine the thermal composition of the fluid flowing through sensed media 105, the thermal conductivity of such fluid can be measured via sensors 104 and 108 and compared to a standard value. This sensing function can also be accomplished by measuring power (i.e., heat) transferred from heater 106 to the sensed media 105. Tubing 116 can be formed from a thin sheet of material that conducts heat/power preferentially in the direction of heater to fluid to sensor so that the heat/power is not wasted by dissipating in other directions.

Tubing 116 can therefore be configured from a film that isolates the fluid (i.e., sensed media 105) from the heater 106, the sensor substrate 102, and sensing elements 104, 108. Such a film conducts heat better through the thin dimension of the film itself rather than either lengths or widths thereof. Such a film can be formed from a low thermal conductivity polymer film plated with metal dots (i.e., not necessarily circular) wherein the polymer material beneath such dots is laser drilled, plasma etched or wet etched (e.g., using photolithography) from underneath such metal, thereby leaving a film with metal dots in a polymer background.

In an alternative embodiment, the aforementioned film can be configured as a thin (e.g., 25 $\mu$m) polymer with a thin metal (e.g., 25 $\mu$m) patterned on opposing sides thereof. Metal can also be configured on a single side thereof, depending upon a desired embodiment. Such a metal can be patterned as lines or dots. The widths and spacing of these features are very small (e.g., (e.g., 5 $\mu$m). Such a thin polymer allows minimal thermal isolation. The metal allows strength and thermal conductivity from the sensor elements to the media. Such an embodiment permits non-precision alignment of the isolation polymer and the sensor heater (e.g., heater 206) and sensing resistors and/or other sensing elements.

The polymer itself can be planar and hydrophilic or hydrophobic (e.g., polyester). The metal can be formed from a bio-compatible metal such as tungsten or platinum. The deposition can be a semiconductor means such as CVD or electro-less plated or sputtered. The space between the metal should also preferably require an insulative fill and be planarized for the media side thereof.

In an alternative embodiment, after laser drilling is performed to create one or more resulting cavities thereof, such cavities can be filled with a high thermal conductivity material such as a metal, typically by electroless plating upward to the polymer surface, thereby providing planarization on the plated side thereof. Such an alternative embodiment can provide strength, improved sealing and an enhanced thermal coupling on the planer side thereof.

Additional embodiments can be implemented by modifying the type of material utilized for sensor substrates 102 and 105. Many applications involving liquid flow sensing require battery operation. The conventional substrate of choice is typically ceramic, which allows some non-efficient means for controlling thermal energy. By implementing a fiberglass base mounting structure, however, in accordance with alternative embodiments of the present invention, energy can be maximized for liquid flow detection and therefore conserved. Thus, sensing substrate 102 can implemented initially in the context of robust liquid flow sensor die and directly mounted and wire bonded on to a fiber glass substrate, commonly known as FR4 or G10 (e.g. approximately 0,5 to 2 mm thick). Thus, substrate 102 can be implemented as fiber glass substrates in accordance with alternative embodiments thereof. A preferred substrate for thermal isolation could be thin (e.g., approximately 1 to 5 mil or 25 to 250 micrometers) flex circuitry, such as, for example, flex circuitry based on a polyimide.

Figure 2:
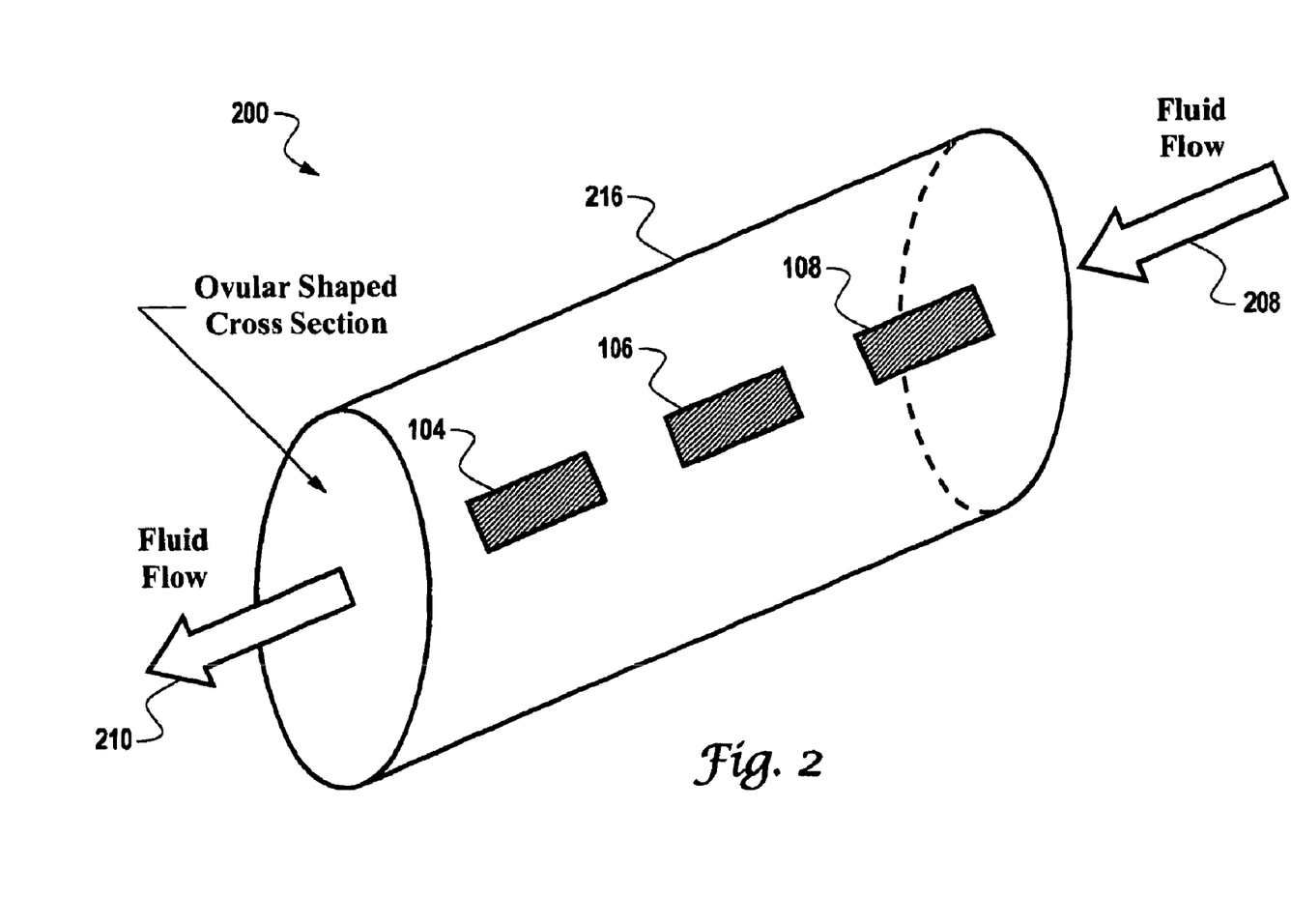
FIG. 2 illustrates a pictorial diagram of a system that includes a flow channel having an ovular shaped cross section, which can be implemented in accordance with an alternative embodiment of the present invention.

FIG. 2 illustrates a pictorial diagram of a system 200 that includes a flow channel 216 having an ovular shaped cross section, which can be implemented in accordance with an alternative embodiment of the present invention. Flow channel 216 is analogous to tubing 116 of FIGS. 1 and 2, the difference being that flow channel 216 possesses an ovular shaped cross section. It can be appreciated, of course, that although an ovular shape is indicated with respect to the alternative embodiment of FIG. 2, other cross sectional shapes can also be implemented in accordance with embodiments of the present invention, such as, for example, a rectangular-shaped cross section. An ovular-shaped cross section is not considered a limiting feature of the present invention. Flow channel 216 of system 200 can be adapted for use with system 100 of FIGS. 1 and 2. Fluid flow is indicated in FIG. 2 by arrows 208 and 210. A plurality of sensing elements 104 and 108 are also depicted in FIG. 2 which are analogous to sensing elements 104 and 108 of FIG. 1.

Conventional flow channels cross the sensing area of sensing elements in a perpendicular direction, such that a small portion on the conventional flow channel circumference aligns with a small portion of the sensor elements. In the configuration of system 200, however, the sensitivity and thermal conduction for a liquid flow sensor can be maximized through an optimized flow channel shape, represented by the ovular cross sectional area of flow channel 216. Conventional flow channels are generally configured in the shape of cylinders with a uniform radius.

Figure 3:
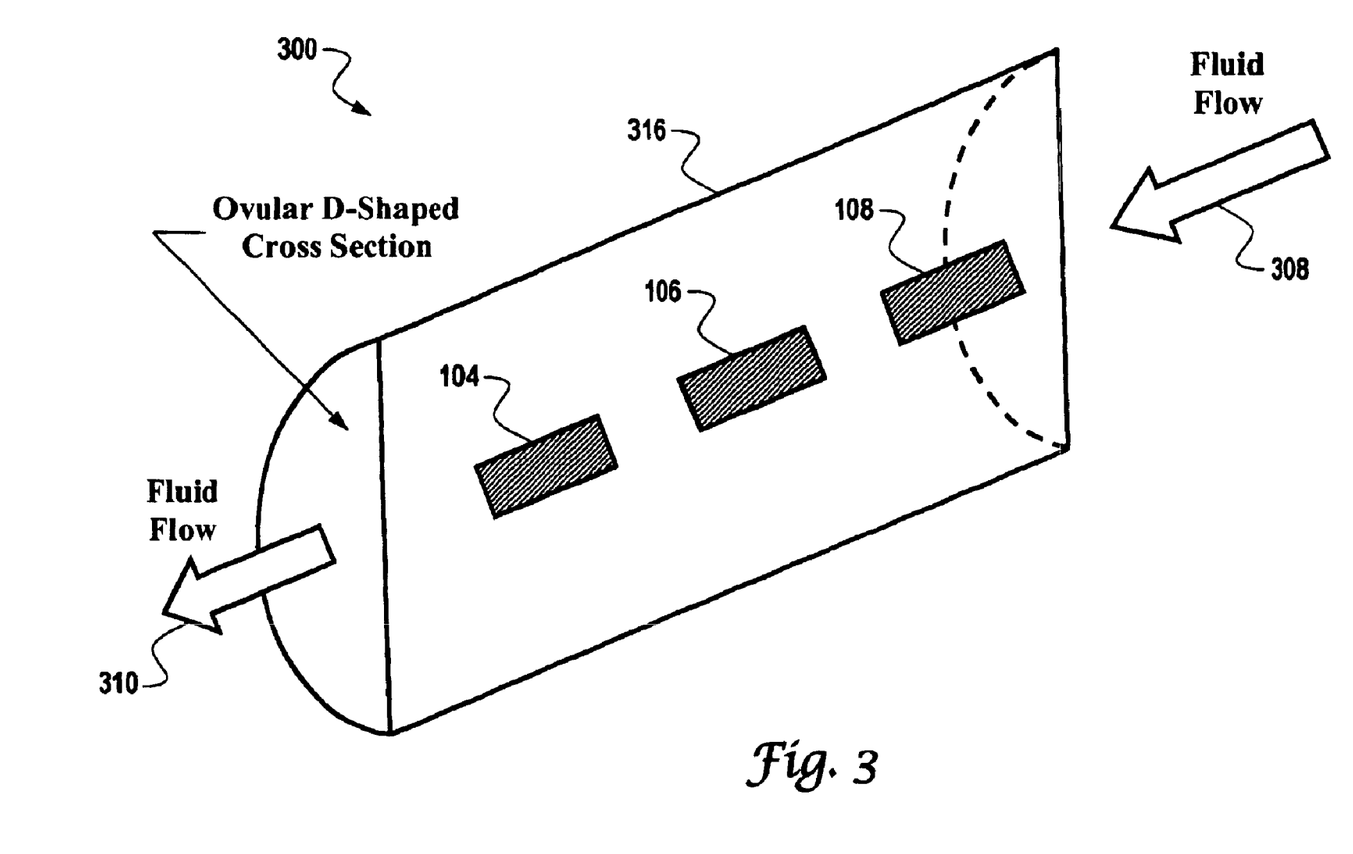
FIG. 3 illustrates a pictorial diagram of a system in which a flow channel comprises an ovular D-shaped cross section that can be implemented in accordance with an alternative embodiment of the present invention.

FIG. 3 illustrates a pictorial diagram of a system 300 in which a flow channel 316 comprises an ovular D-shaped cross section that can be implemented in accordance with an alternative embodiment of the present invention. Note that in FIGS. 1-3, identical or analogous parts are indicated by identical reference numerals. Thus, in system 300, sensing elements 104 and 108 are located at the "flat side" of the "D" shaped ovular cross section. Fluid flow is indicated in FIG. 3 by arrows 308 and 110. Thus, a preferred "oval" type cross section is a "D" shaped cross section where the flat side of the "D" is in contact with active sense elements 104, 108. A heater 106 is generally located between sense elements 104 and 106. In an alternative embodiment, heater 106 can be replaced with a sense element and moved to a different location along the flat portion of the "D" shaped cross section of flow channel 316.

Flow channel 216, on the other hand, comprises an oval cross section flow channel that covers a larger surface area of the sensor sensing elements 104', 106, and 108. Such a configuration generally provides a large width to height ratio of, for example, a 5:1 ratio. Additionally, the sensor side of the flow channel can be provided with as thin as possible a thickness to maximize the thermal conductivity from the media to the sensor elements. Sensitivity can therefore be maximized by utilizing more width space along flow channel 315 rather than length space. Flow channel 216 can be molded or extruded, and the material utilized to form flow channel 216 can be metal, fused silica, Radel 5000, a polymer and so forth. Flow channel 216 can be applied to sensing elements 104, 106, and 108 with a thermally conducting fluid to further maximize thermal conductivity.

The disclosed embodiments can be implemented a number of applications, including medical applications involving the use of fluids such as saline and other medical fluids. One example where alternative embodiments can be implemented is in the context of a so-called "time of flight" type sensor, wherein a heat pulse is generated by heater 106. Time can then be measured from the initiation of the heat pulse until a thermal spike is sensed at sensing elements 104 and/or 108. An example of a "time of flight" type: sensor is disclosed in U.S. Pat. No. 6,234,016, "Time lag approach for measuring fluid velocity," which issued to Ulrich Bonne et al on May 22, 2001. U.S. Pat. No. 6,234,016, which is incorporated herein by reference, discloses a method and apparatus for measuring the velocity of a fluid relatively independently of the physical properties of the fluid.

Figure 4:
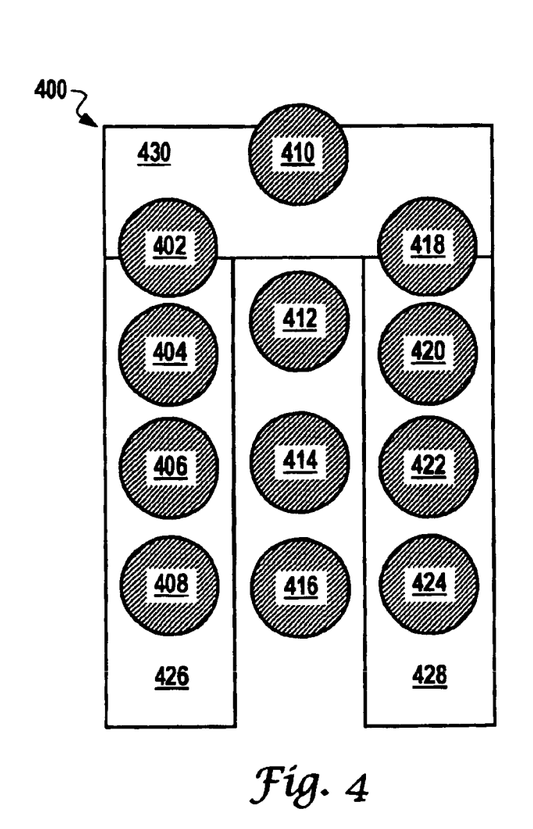
FIG. 4 illustrates a top view of a metal dot pattern which can be implemented in accordance with a preferred embodiment of the present invention.

FIG. 4 illustrates a top view of a metal dot pattern 400 which can be implemented in accordance with a preferred embodiment of the present invention. Metal dot pattern 400 can be configured to form a plurality of particles such as those illustrated herein with respect to FIG. 1. Thus, in FIG. 4, a plurality of metal dots 402–424 are depicted patterned over layers 426, 428 and 430. The dots 402–424 can be sized with diameters of approximately 4 $\mu$m. Dots 402–424 can also be spaced approximately 5 $\mu$m from one another.

Figure 5:
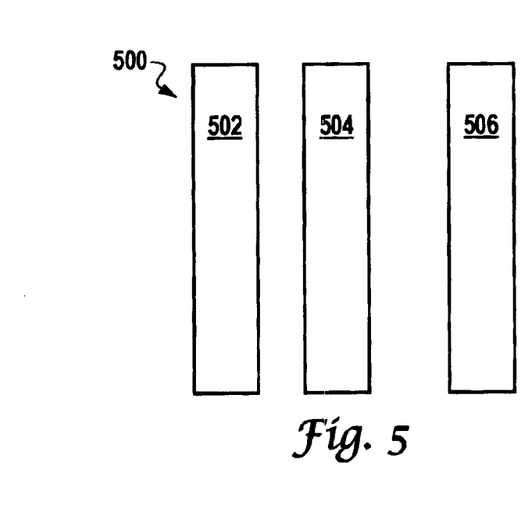
FIG. 5 illustrates a top view of a metal line pattern, which can be implemented in accordance with an alternative embodiment of the present invention.

Dots 402–424 comprise metal conductors as indicated herein. Note, however, that such metal conductors can also be configured according to other shapes. For example, FIG. 5 illustrates a top view of a metal line pattern 400, which can be implemented in accordance with an alternative embodiment of the present invention. Instead of forming dots, the metal conductors can be patterned as metal lines 502, 504, and 506.

Figure 6:
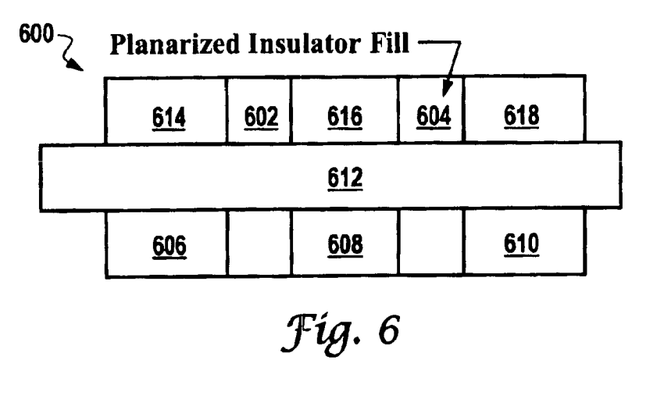
FIG. 6 illustrates a side view of a metal pattern configuration, in accordance with an alternative embodiment of the present invention.

FIG. 6 illustrates a side view of a metal pattern configuration 600, in accordance with an alternative embodiment of the present invention. FIG. 6 depicts a side view of a "sandwich" configuration in which a poly layer of approximately 25 $\mu$m is disposed between metal layers 614, 616, 618 and 606, 608, 610, which can also have a width of approximately 25 $\mu$m. Planarized insulator fill layers 602 and 604 can also be located respectively between metal layers 614, 606 and 616, 608 and 618, 610. Metal layers 614, 616, 618 and 606, 608, 610 can be formed as dots (i.e., see FIG. 4) or lines (i.e., See FIG. 5), depending upon a desired embodiments. Metal layers 614, 616, 618 and 606, 608, 610 can also be formed into other patterns, such as a grid pattern of metal conductors. The metal conductors can thus have various shapes. In general, the dimensions of the dot or lines formed thereof should be less than the conductor or spacing thereof, whichever is smaller.

Figure 7:
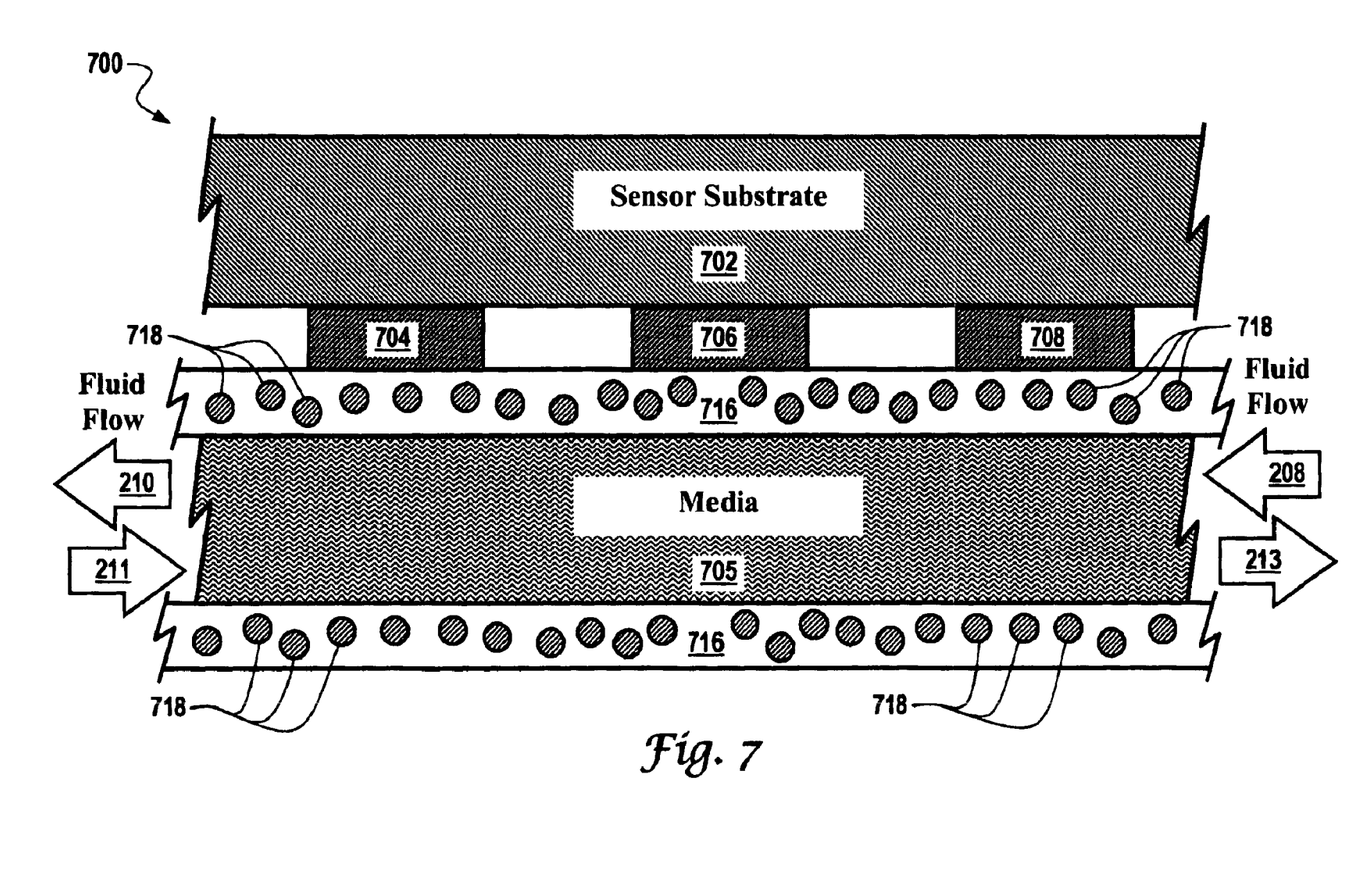
FIG. 7 illustrates a block diagram of a sensor system at time which can be implemented in accordance with a preferred embodiment of the present invention.

FIG. 7 illustrates a block diagram of a sensor system 700, which can be implemented in accordance with a preferred embodiment of the present invention. System 700 is analogous to system 100 of FIG. 1, except that the thicknesses of the respective components vary. Also, the general configuration of system 700 is modified in comparison to that of system 100 of FIG. 1. System 700 of FIG. 7 generally comprises a low thermal conductivity tubing 716 with a plurality of thermally conductive particles 718 located within the walls of tubing 716. A plurality of sensing elements 704 and 708 can be disposed along a sensor substrate 702. Tubing 716 can be configured to surround media 705 for sensing thereof. Although a single sensor substrate 702 and sensed media 705 are depicted in system 700 of FIG. 7, it can be appreciated that alternative embodiments thereof can be configured to function with one or more such sensor substrates and one or more sets of associated sensor elements.

Sensed media 705 can be, for example, a liquid such as saline or another equivalent medical fluid utilized in medical applications. The fluid flow, represented by arrows 208 and 210 is generally co-linear with the sensed media 705. Element 706 can be, in a particular embodiment, a heater or a sensing element co-located with sensing elements 704 and 708. Elements 704, 706 and 708 can thus be implemented as sense resistors. Assuming that element 706 is a heater, heat can then transfer from heater 706 through thermally conductive particles 718 to the fluid sensed (i.e., sensed media 705).

Note that elements 704, 706, and 708 of FIG. 7 are generally analogous to elements 104, 106, and 108 of FIG. 1. Similarly, sensor substrate 702 of FIG. 7 is analogous to sensor substrate 102 of FIG. 7. Likewise, media 705 of FIG. 7 is similar to that of media 105 of FIG. 1. Particles 718 are analogous to particles 118, and tubing 716 is analogous to tubing 116. Sensor substrate 702 can comprise a thickness, for example, of approximately 500 $\mu$m. Sensed media 705 can possess an internal diameter of approximately 100 $\mu$m. The thickness of the walls of tubing 716 can be approximately 25 $\mu$m. On the other hand, elements 704, 706, and 708 can each have a thickness of approximately 0.1 $\mu$m.

Heat can be conducted through the fluid to other conductive particles that are in contact with the sensing resistors or sensing elements 704, 708. The heat is finally conducted through such particles to elements 704 and 708 at which point the heat is sensed and a flow signal generated. It can be appreciated that although FIG. 7 illustrates the use of element 706 (e.g. a heater and/or sensing element), the configuration of FIG. 7 can be implemented without element 706, in which case elements 704 and 708 can implemented as self-heated elements, which can cool at different rates dependent on flow.

When there is no flow, however, elements 704 and 708 can obtain the same amount of heat and their signal difference becomes a zero value. If flow is present from right to left, as indicated by arrows 208 to 210, then the sensor or sensing element 708 is cooler than that of sensing element 704. A difference signal is therefore present, which is proportional to mass flow. Note that in FIG. 7, fluid flow can be bi-directional. In one implementation, fluid flow can be from right to left, respectively from arrow 208 to 210. In an alternative embodiment, fluid flow can be from left to right, respectively from arrow 211 to 213.

Each particle diameter of the plurality of thermally conductive particles 718 is approximately equivalent to the wall thickness of the walls of tubing 716. Such particles are gathered in a high percentage, such that they do not generally come into physical contact with one another. Thus, thermal conduction radially is very much higher than thermal conductivity in the longitudinal or circumferential directions thereof. The base tubing 716 can be formed from a low thermal conductivity non-silicone plastic material. In alternative embodiment, silicone material may function, but will have a lower efficiency due to its relatively high thermal conductivity. Thus, non-silicone plastic material is preferred.

The particles 718 possess a high thermal conductivity and a low electrical conductivity. Particles 718 can be formed from materials such as, but not limited to, diamond or crystalline ceramic material. Anodized aluminum or other oxidized metals can be utilized to form such particles 718. Electrically conductive particles can also be utilized in place of particles 718, but are generally not preferred because such particles may react with fluid flowing through tubing 716 or leak electricity into undesired areas.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

The embodiments of the invention in which an exclusive property or right is claimed are defined as follows.

Having thus described the invention what is claimed is:

1. A sensor method, comprising the steps of:
   providing a sensor for measuring a thermal conductivity of a fluid, wherein said sensor comprises at least one fluid sensing element associated with a sensor substrate;
   associating a heater with said sensor wherein said heater provides heat to said fluid; and
   providing a film component that isolates said fluid from said heater and said sensor, such that said film component conducts heat in a direction from said heater to said sensor, thereby forming a thermal coupling between said sensor, said heater and said fluid, which permits said sensor to determine a composition of said fluid by measuring thermal conductivity thereof without undesired losses of heat in other directions.

2. The method of claim 1 further comprising the step of configuring said film component to comprise a tubing composed of at least one wall have a wall thickness thereof, wherein a plurality of thermally conductive particles are dispersed within said at least one wall of said tubing.

3. The method of claim 2 further comprising the step of configuring each particle of said plurality of thermally conductive particles to comprise a particle diameter that is approximately equivalent to said wall thickness.

4. The method of claim 2 further comprising the step of forming said tubing from a plastic, such that said plurality of thermally conductive particles possesses a high thermal conductivity and said plastic possesses a lower electrical conductivity.

5. The method of claim 2 further comprising the step of forming said plurality of thermally conductive particles from diamond.

6. The method of claim 2 further comprising the step of forming said plurality of thermally conductive particles comprises particles from crystalline ceramic materials.

7. The method of claim 2 further comprising the step of forming said plurality of thermally conductive particles from anodized aluminum.

8. The method of claim 2 further comprising the steps of:
   configuring said film component from a low thermal conductivity polymer;
   associating a metal with said low thermal conductivity polymer;
   etching said metal located below said low thermal conductivity polymer to form a plurality of metal dots upon said low thermal conductivity polymer, thereby providing said film component with said plurality of metal dots plated in a polymer background thereof, such said plurality of metal dots comprise said plurality of thermally conductive particles.

9. The method of claim 2 further comprising the steps of:
configuring said film component from a low thermal conductivity polymer;
associating a metal with said low thermal conductivity polymer;
laser drilling said low thermal conductivity polymer to form a cavity therein; and
thereafter filling said cavity with metal up to a surface of said polymer to provide planarization to a plated side of said polymer, such said plurality of metal dots comprises said plurality of thermally conductive particles.

10. The method of claim 1 further comprising the step of configuring said sensor to comprise a sensor die mounted and wire bonded to said sensor substrate, wherein said sensor substrate provides a low thermal conductivity base mounting structure wherein energy thereof is maximized for liquid flow detection.

11. The method of claim 1 further comprising the step of configuring said film component to comprise a flow channel having an oval cross sectional area thereof that covers a majority surface area of said at least one sensing element of said sensor.

12. The method of claim 1 further comprising the step of configuring said film component to comprise a flow channel having a "D" shaped cross sectional area thereof that covers a majority surface area of said at least one sensing element of said sensor.

13. A sensor method, comprising the steps of:
providing a sensor for measuring a thermal conductivity of a fluid, wherein said sensor comprises at least one fluid sensing element;
configuring said sensor from a sensor die mounted and bonded to a fiber glass substrate, thereby providing a fiberglass base mounting structure wherein energy is maximized for liquid flow detection;
associating a heater with said sensor wherein said heater provides heat to said fluid;
providing a film component that isolates said fluid from said heater and said sensor, such that said film component conducts heat in a direction from said heater to said sensor, thereby forming a thermal coupling between said sensor, said heater and said fluid, which permits said sensor to determine a composition of said fluid by measuring thermal conductivity thereof without undesired losses of heat in other directions;
configuring said film component to comprise a tubing composed of at least one wall have a wall thickness thereof, wherein a plurality of thermally conductive particles are dispersed within said at least one wall of said tubing;
configuring each particle of said plurality of thermally conductive particles to comprise a particle diameter that is approximately equivalent to said wall thickness; and
forming said tubing from a plastic, such that said plurality of thermally conductive particles possesses a high thermal conductivity and a low electrical conductivity.

14. A sensor system, comprising:
a sensor for measuring a thermal conductivity of a fluid, wherein said sensor comprises at least one fluid sensing element associated with a sensor substrate;
a heater for providing heat to said fluid; and
a film component that isolates said fluid from said heater and said sensor, such that said film component conducts heat in a direction from said heater to said sensor, thereby providing a thermal coupling between said sensor, said heater and said fluid, which permits said sensor to determine a composition of said fluid by measuring thermal conductivity thereof without undesired losses of heat in other directions.

15. The system of claim 14 wherein said film component comprises a film composed of at least one wall have a wall thickness thereof, wherein a plurality of thermally conductive particles are dispersed within said at least one wall of said film.

16. The system of claim 15 wherein each particle of said plurality of thermally conductive particles comprises a particle diameter that is approximately equivalent to said thickness.

17. The system of claim 15 wherein said film comprises plastic, such that said plurality of thermally conductive particles possess a high thermal conductivity and a low electrical conductivity.

18. The system of claim 15 wherein said plurality of thermally conductive particles comprises particles formed from at least one of the following materials: diamond, crystalline ceramic, and anodized aluminum.

19. The system of claim 15 wherein said film component comprises a low thermal conductivity polymer plated with a plurality of metal dots, wherein said plurality of metal dots are formed by patterning said low thermal conductivity polymer and thereafter providing an etch upon a metal associated with said low thermal conductivity polymer to thereby provide said film component with said plurality of metal dots in a polymer background thereof, such said plurality of metal dots comprise said plurality of thermally conductive particles.

20. The system of claim 15 wherein said film component comprises a low thermal conductivity poly er plated with a plurality of metal dots, wherein said plurality of metal dots are formed by laser drilling said low thermal conductivity polymer to form a cavity thereof and thereafter filling said cavity with metal up to a surface of said polymer to provide planarization to a plated side of said polymer, such said plurality of metal dots comprise said plurality of thermally conductive particles.

21. The system of claim 14 wherein said sensor comprises a sensor die mounted and bonded to said sensor substrate, wherein said sensor substrate comprises a low thermal conductivity base mounting structure wherein energy transfer thereof is maximized for liquid flow detection.

22. The system of claim 14 wherein said film component comprises a flow channel having an oval cross sectional area thereof that covers a majority surface area of said at least one sensing element of said sensor and wherein said flow channel is applied to said at least one sensing element utilizing a thermally conducting fluid to maximize thermal conductivity.

* * * * *